(12) United States Patent
Lobman (10) Patent No.: US 11,462,317 B2
(45) Date of Patent: Oct. 4, 2022

(54) METHOD AND SYSTEM FOR DISPLAYING MEDICAL CLAIM INFORMATION

(71) Applicant: QVH SYSTEMS, LLC, Tulsa, OK (US)

(72) Inventor: Alexander Lobman, Tulsa, OK (US)

(73) Assignee: QVH Systems, LLC, Tulsa, OK (US)

( * ) Notice: Subject to any disclaimer, the term of this patent is extended or adjusted under 35 U.S.C. 154(b) by 303 days.

(21) Appl. No.: 16/550,568

(22) Filed: Aug. 26, 2019

(65) Prior Publication Data
US 2020/0075156 A1 Mar. 5, 2020

Related U.S. Application Data

(60) Provisional application No. 62/724,801, filed on Aug. 30, 2018.

(51) Int. Cl.
| | |
|---|---|
| *G16H 40/20* | (2018.01) |
| *G06Q 40/08* | (2012.01) |
| *G06Q 30/04* | (2012.01) |
| *G16H 40/60* | (2018.01) |
| *G16H 10/60* | (2018.01) |
| *G06Q 10/10* | (2012.01) |

(52) U.S. Cl.
CPC .............. *G16H 40/20* (2018.01); *G06Q 30/04* (2013.01); *G06Q 40/08* (2013.01); *G06Q 10/10* (2013.01); *G16H 10/60* (2018.01); *G16H 40/60* (2018.01)

(58) Field of Classification Search
CPC ........ G16H 40/20; G16H 40/60; G16H 10/60; G16H 10/10; G06Q 30/04
USPC .......................................................... 705/2–3
See application file for complete search history.

(56) References Cited

U.S. PATENT DOCUMENTS

| | | | | |
|---|---|---|---|---|
| 2004/0122704 | A1* | 6/2004 | Sabol | G16H 30/20 705/2 |
| 2005/0171817 | A1* | 8/2005 | Sachdev | G16H 50/20 705/3 |
| 2005/0215867 | A1* | 9/2005 | Grigsby | G16H 40/20 600/300 |
| 2010/0131293 | A1* | 5/2010 | Linthicum | G16H 10/60 705/3 |
| 2011/0184760 | A1* | 7/2011 | Shen | G06Q 10/10 705/3 |

(Continued)

*Primary Examiner* — Michael Tomaszewski
(74) *Attorney, Agent, or Firm* — Saul Ewing Arnstein & Lehr LLP (57) ABSTRACT

Methods, systems, and computer-readable media for displaying a graphical representation of patient form information are described herein. The method can include receiving a plurality of digital patient forms from at least one medical feed source, where each digital patient form comprises a set of medical data for a medical patient, determining at least a portion of medical data from the plurality of digital patient forms is associated with a predefined medical parameter, where the predefined medical parameter is different than a temporal parameter, generating a graphical medical history of the at least a portion of medical data, the graphical medical history organized by a categorical variable axis and providing a visual indicator of the association between the at least a portion of medical data and the predefined medical parameter temporally spanning across the plurality of digital patient forms, and displaying the graphical medical history via a GUI to a user.

19 Claims, 7 Drawing Sheets

(56) References Cited

U.S. PATENT DOCUMENTS

2014/0136237 A1\* 5/2014 Anderson .............. G06Q 10/10
705/3

\* cited by examiner

METHOD AND SYSTEM FOR DISPLAYING MEDICAL CLAIM INFORMATION

CROSS-REFERENCE TO RELATED APPLICATION

This application claims priority to U.S. Provisional Patent Application Ser. No. 62/724,801 filed Aug. 30, 2018. The entire content of this application is hereby incorporated by reference herein.

BACKGROUND OF THE INVENTION

A major issue existing within the healthcare industry is how to provide higher quality healthcare with better health results, while simultaneously lowering costs for patients. Unfortunately, efforts to reign in healthcare costs over the last several decades have largely been unsuccessful. For example, healthcare professionals are skeptical of clinical guidelines due to the disparity between patients and the complexity of their various clinical presentations. Prior authorization programs impose delays in treatment implementation and can be costly to administer. Audit and recoupment systems are also administratively costly and can create friction within the healthcare professional-payer relationship. Further, due to the ubiquity of the third-party payer financial system, both patients and healthcare professionals have little financial exposure to the treatment decisions that are made. Patients and healthcare professional generally have minimal knowledge on how much a treatment choice will cost, nor do patients and healthcare professionals have the ability to comprehensively view the clinical or financial results for a patient.

Indeed, there is virtually no transparency to the healthcare workforce or their patients as to what their healthcare choices cost. By virtue of the orders that the healthcare professional writes, an ordering professional may be responsible for generating most of a patient's healthcare costs. That professional often receives little, if any, feedback on what occurs after the referral is made. In addition, there are often others who provide or order services of which the patient's healthcare professional is completely unaware. Patients, on the other hand, may not appreciate the clinical implications of each separate service, and they generally lack the knowledge of what their treating healthcare professionals and facilities are paid. While third-party payers are able to view this data comprehensively, they do not have the expertise of the healthcare professionals related to the patient population or local resource constraints, nor the experience to translate the contained data into actionable information for healthcare professionals.

There is a need for an automated system and method enabling healthcare professionals and patients to view in a comprehensible way what happens once treatment decisions are made.

SUMMARY

The claimed invention generates and displays comprehensive graphical representations that provide healthcare professionals and patients with a full understanding of healthcare treatment choices. Forms data contains a wealth of information. This forms data include detailed patient and provider demographics, as well as payment amounts. When viewed as an individual patient medical history, it provides a comprehensive view of the specific services received, as well as potentially unexpected consequences of those services. When form data is viewed across a patient population, it can provide healthcare professionals a clear picture of the relative efficiency of their various referral options. It also allows those engaged in utilization review and healthcare professionals the opportunity to view similar patient as one another, which can lead to more beneficial conversations between healthcare providers and third-party payers.

These comprehensive graphical representations also enable healthcare professionals and patients to visualize a medical prognosis, including potential alternative results. These results can be enhanced by providing a potential future trend of prognoses and proposed medical treatment plans. Additionally, the graphical representations can illustrate an easy and clear comparison of actual results of a prognosis, potentially allowing for timely course correction should that be appropriate.

In certain aspects, the claimed invention provides a method for displaying a comprehensive graphical representation of patient form information. The method can include receiving a plurality of digital patient forms from at least one medical feed source, where each digital patient form comprises a set of medical data for a medical patient, determining at least a portion of medical data from the plurality of digital patient forms is associated with a predefined medical parameter, where the predefined medical parameter is different than a temporal parameter, generating a graphical medical history of the at least a portion of medical data, the graphical medical history organized by a categorical variable axis and providing a visual indicator of the association between the at least a portion of medical data and the predefined medical parameter temporally spanning across the plurality of digital patient forms, and displaying the graphical medical history via a graphical user interface (GUI) to a user.

The method can include a variety of embodiments. In some cases, the visual indicator includes a color or an object shape. In some cases, the graphical medical history includes a Gantt graph.

In one embodiment, the method can include receiving input from the user selecting the predefined medical parameter, where the determining is based at least in part on the received input. In some cases, the predefined medical parameter includes a type of medical condition, a type of diagnosis, a type of medical service, a type of medical service provider, a medical prognosis, or a combination thereof. In some cases, the user includes the patient, a health care provider, an insurance provider representative, an authorized user for the health care provider, an authorized user for a health care provider organization, or an authorized user for the patient.

In one embodiment, the method can include receiving a second plurality of digital patient forms including a second set of medical data for another medical patient, determining at least a portion of the second set of medical data is associated with the predefined medical parameter, and where the graphical medical history further provides a visual indicator of the association between the at least a portion of the second set of medical data and the predefined medical parameter temporally spanning across the second plurality of digital patient forms.

In one embodiment, the method can include receiving at least one additional digital patient form from the at least one form feed source, and updating the graphical medical history of the at least a portion of medical data based on the at least one additional digital patient form.

In one embodiment, the method can include identifying a format of the received plurality of digital patient forms, extracting the medical data from the plurality of digital patient forms based at least in part on the identified format, and storing the medical data.

One aspect of the claimed invention includes a system for displaying a comprehensive graphical representation of patient form information. In one embodiment, the system can include a form data storage component in electronic communication with at least one form feed source, the form data storage component configured to receive a plurality of digital patient forms from the at least one form feed source, where each digital patient form comprises a set of medical data for a medical patient, a form analysis component configured to: determine at least a portion of medical data from the plurality of digital patient forms is associated with a predefined medical parameter, and generate a graphical medical history of the at least a portion of medical data, the graphical medical history organized by a categorical variable axis and providing a visual indicator of the association between the at least a portion of medical data and the predefined medical parameter temporally spanning across the plurality of digital patient forms, and a graphical user interface (GUI) configured to display the graphical medical history to a user.

The system can include a variety of embodiments. In some cases, the visual indicator includes a color, an object shape, or text. In some cases, the graphical medical history further includes a Gantt graph.

In one embodiment, the form analysis component is further configured to receive input from the user selecting the predefined medical parameter, where the determining is based at least in part on the received input.

In some cases, the predefined medical parameter includes a type of medical condition, a type of diagnosis, a type of medical service, a type of medical service provider, a medical prognosis, or a combination thereof. In some cases, the user comprises the patient, a medical provider, an insurance provider representative, an authorized user for the health care provider, an authorized user for a health care provider organization, or an authorized user for the patient.

In one embodiment, the form analysis component is further configured to receive a second plurality of digital patient forms comprising a second set of medical data for another medical patient, determine at least a portion of the second set of medical data is associated with the predefined medical parameter, and where the graphical medical history further provides a visual indicator of the association between the at least a portion of the second set of medical data and the predefined medical parameter temporally spanning across the second plurality of digital patient forms.

One aspect of the invention includes a non-transitory computer readable medium for displaying a comprehensive graphical representation of patient form information. In one embodiment, the computer readable medium includes computer readable program code that, when executed, causes a processor to: receive a plurality of digital patient forms from at least one form feed source, where each digital patient form comprises a set of medical data for a medical patient, determine at least a portion of medical data from the plurality of digital patient forms is associated with a predefined medical parameter, generate a graphical medical history of the at least a portion of medical data, the graphical medical history organized by a categorical variable axis and providing a visual indicator of the association between the at least a portion of medical data and the predefined medical parameter temporally spanning across the plurality of digital patient forms, and display the graphical medical history via a graphical user interface (GUI) to a user.

This aspect of the invention can have a variety of embodiments. In some cases, the visual indicator includes a color, an object shape, or text. In some cases, the graphical medical history further includes a Gantt graph.

In one embodiment, the computer readable program code is further executable to receive input from the user selecting the predefined medical parameter, where the determining is based at least in part on the received input.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

The invention described herein automates and makes transparent an important aspect of a health care professional's clinical practice in a fashion that is not currently available to them. The graphical representation enables health care professionals, at a glance view, to understand a patient's clinical course of care and its costs, and to share that picture with the patient to help the patient make more knowledgeable decisions. It makes much more sense to provide clinicians and their patients with a full understanding of their choices and their outcomes than to continue the complex, costly and unsuccessful utilization review systems described above. When viewed as an individual patient medical history, the invention provides a comprehensive view of the specific services received, as well as the potentially unexpected consequences of those services and their sequelae. When viewed for a patient population, the graphical representation provides the clinicians who made the referrals a clear picture of the relative efficiency of their various referral options, in the context of available resources and their patients' needs. The graphical representation also allows those engaged in utilization review the opportunity to look the individual patient histories comprising what were formerly seen as consolidated "areas of concern," thus allowing engagement of the treating clinicians in a meaningful conversation rather than simply subjecting them to adversarial pronouncements.

As personalized medicine and artificial intelligence provide evermore data points to factor in to clinical decision-making, there is also a need for an automated system and method enabling clinicians and their patients, to visualize the prognosis, including the potential alternative results. These results will be more meaningful if they are displayed as an extension of the patient's actual medical history, using the graphical representation described above, but then trended into the future. This graphical representation also provides a clear method of comparing the actual results to the prognosis, potentially allowing for timely course correction should that be appropriate.

Figure 1:
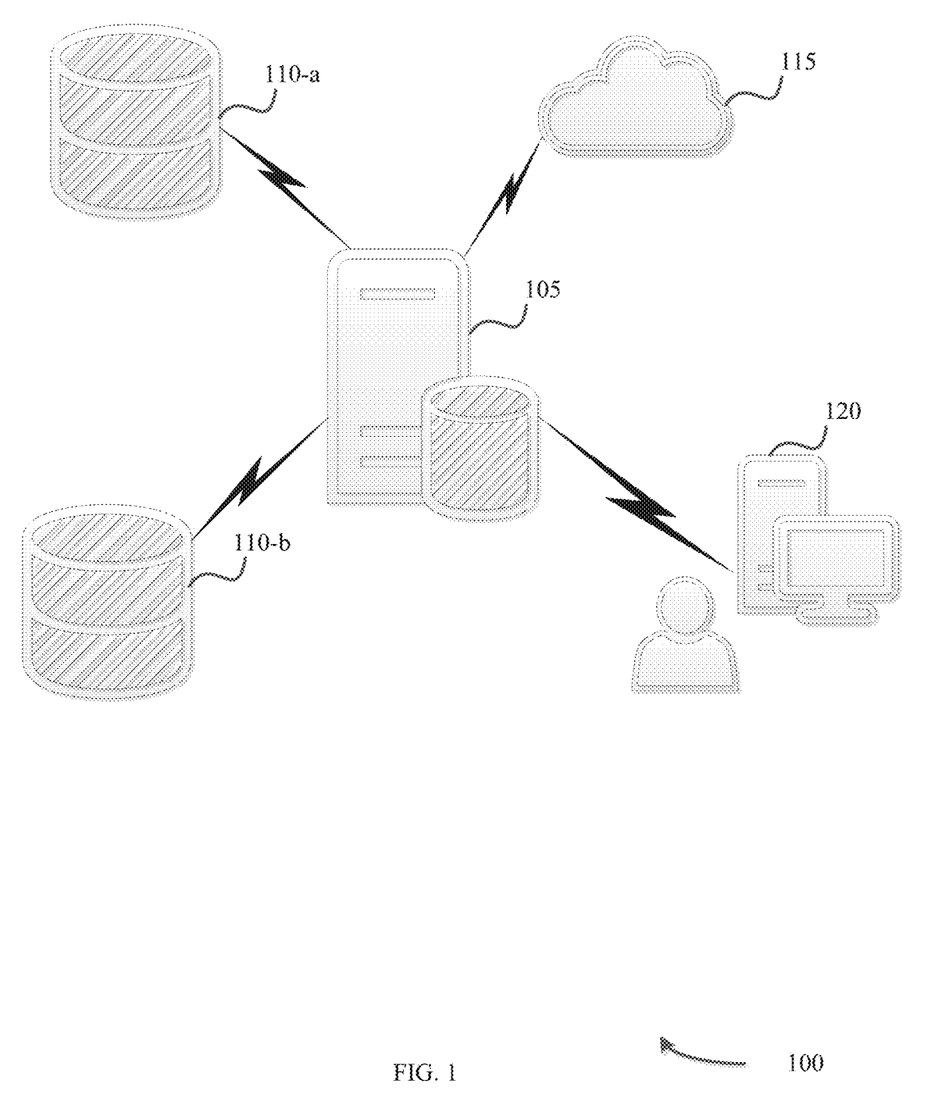
FIG. 1 depicts a system for displaying medical form information according to an embodiment of the claimed invention.

FIG. 1 illustrates a system 100 for displaying medical form information, according to an embodiment of the claimed invention. The system 100 can include a form warehouse 105, one or more form feed sources 110-*a* and 110-*b*, a cloud network 115, and a user device 120.

The one or more form feed sources 110-*a* and 110-*b* can be databases which contain patient medical forms. In some cases, a patient medical form can be a medical claim from a health care provider for a third-party payer to pay for specified medical treatments (e.g., HIPAA standard transaction 837), or a remittance advice a third-party payer returns to the health care provider related to how a medical claim was paid (e.g., HIPAA standard transaction 835). The patient medical forms can contain a variety of data, such as patient personal information (e.g., name, address, age, sex, race, ethnicity, other various social determinants of health factors, preferences, experiences, outcomes, contact information, social security number, identification number, and the like), medical diagnoses, medical prognoses, treatment or testing services, drugs, supplies, other health care services the patient has received and/or associated costs, lab values, treatment outcomes, healthcare professional information, third party payer information, or a combination thereof. Further, patient form information can include, without limitation, the information contained in a HIPAA standard transaction 837, 835, 278 or other electronic standard transaction claim, payment or eligibility form or other electronic exchange of information to carry out financial or administrative activities related to health care, a Consolidated Clinical Document (CCD) or other Electronic Health Record (EHR) export, a patient demographic or satisfaction survey result or other collections of information relevant to a patient's health care. In some cases, a patient medical form can be transmitted to a third-party payer to request payment for a requested treatment (e.g., an 837 claim), where the third-party payer can subsequently return a remittance advice (e.g., an 835 form) and then store the information in patient medical forms in a form feed source, such as form feed source 110-*a*.

The form feed source 110-*a* and/or 110-*b* can be managed or owned by a variety of health care providers, third-party payers, or entities. For example, form feed source 110-*a* can be managed or owned by Medicare. Thus, the form feed source 110-*a* can process and/or store medical forms received by Medicare, such as Medicare's Claim and Claim Line Feed (CCLF), Health Insurance Portability and Accountability Act (HIPAA) standard health claims, remittance advice, other electronic transactions, Centers for Medicare and Medicaid Services (CMS) Blue Button Explanation of Benefits, related Fast Healthcare Interoperability Resources (FHIR) feeds, or a combination thereof. Additionally or alternatively, form feed source 110-*b* can be managed or owned by private third-party payers, insurers, clearing houses acting as intermediaries between health care providers and third-party payers, etc. Form feed source 110-*b* can thus process and/or store medical forms received or created by private third-party payers or insurers. Form feed sources 110-*a* and 110-*b* can be in wired or wireless communication with form warehouse 105. In some cases, form feed sources 110-*a* and 110-*b* can be in wired or wireless communication with one another. Further, form feed sources 110-*a* and 110-*b* can transmit processed/stored medical form data to the form warehouse via automatically in a periodic fashion, or prompted (e.g., via a push or pull mechanism).

The form warehouse 105 can receive the medical forms or medical forms data from the form feed sources 110-*a* and/or 110-*b*. In some cases, the form warehouse 105 can determine or identify a format of the medical form received from the transmitting form feed source. Based on the determination or identification, the form warehouse 105 can then extract medical form data from the received medical form(s). The form warehouse 105 can subsequently store the received medical forms or medical forms data.

The form warehouse 105 can aggregate medical form data based on receiving a set of inputs from a user device 120. The form warehouse 105 can receive a request to generate a graphical representation of medical form data. The request in some cases can be associated with a patient identifier (e.g., based on user login information for communicating with the form warehouse 105, etc.) or a group of patients. The form warehouse 105 can search through stored form data to determine or identify form data associated with the patient identifier or group of patients. The data warehouse can then "pull" the determined or identified form data associated with a patient or patients to generate a graphical representation of the form data.

The form warehouse 105 can also identify other associations between medical form data and various other parameters. For example, the generation request can also include a set of predefined parameters. These predefined parameters can be "categories" of medical data, such as dates, types of services, prognoses, diagnoses, service location, and the like. The predefined parameters can be selected by a user (e.g., communicated via the generation request), or alternatively be selected prior to the request (e.g., as standard format parameters). The data warehouse can search through the pulled form data of a patient or patients and determine or identify an association between a set of form data and one or more predefined parameters.

The form warehouse 105 can then generate a graphical representation of the data results. The graphical representation can be generated in such a way so as to depict medical history across the span of the forms stored for the identified patient or patients. For example, the medical form data can be presented in a chronological fashion (e.g., the horizontal axis is time). The vertical axis can be a predefined parameter, such as disease type, etc. In some cases, the vertical axis can be a discrete axis, where the axis is partitioned into separate categories. Alternatively, the vertical axis can be a continuous axis. The initial parameter for the vertical and/or the horizontal axis can in some cases be modified based on user input. In some cases, the graphical representation can be a Gantt graph.

The graphical representation can generate visual indicators for displaying the association between the data results and predefined parameters. The visual indicators can be a shape (e.g., a horizontal bar, a triangle, a circle, etc.), a color (a red line, a blue bar, etc.), numerical value, text, or the like. The visual indicator can indicate that a data point exists at that location of the graphical representation, and can also indicate the association the data point has with a predefined parameter. Additional examples of the visual indicators are provided in the examples discussed below.

The form warehouse 105 can transmit the generated graphical representation to the user device 120, another device (not shown), or to a connected display (e.g., a graphical user interface (GUI)) to display the graphical representation.

The visual indicators can provide additional information regarding the medical form data. For example, in some cases the visual indicators may include a hovering feature attached to the visual indicator. A user can hover a mouse pointer icon over the visual indicator. After a predefined period of time, an additional information box can be displayed. The additional information box an include additional information associated with the medical form data over which the pointer icon is hovering (e.g., data of the associated medical form or date of patient treatment, type of treatment, cost of treatment, attending physician, location of treatment, etc.). Additionally or alternatively, the visual indicator can be selected or "clicked" by a pointer icon to display the information box.

In some cases, the form warehouse can receive additional input from the user device 120. In some cases, the form warehouse 105 can transmit a query for additional information, such as additional predefined parameters for the graphical representation. In other cases, the additional input containing additional predefined parameters can be initiated from the user side (e.g., user device 120). The form warehouse 105 can receive the predefined parameters and can search through stored form data to determine or identify form data associated with a requested predefined parameter. For example, the user device 120 can transmit a request for a graphical representation containing medical form data that is associated with a disease type. The form warehouse 105 can search through the stored form data and determine that a set of data stored is associated with the disease type. The form warehouse 105 can then process the set of data to generate the graphical representation.

Various predefined parameters can be available for a user device 120 to select. Some examples can include patient identifier, a patient type (e.g., a demographic value, etc.) a specified time period, a prognosis type, a diagnosis type, a treatment type, a cost value or type, treatment location (e.g., a specific hospital, a specific type of treatment facility, etc.), a treatment provider type (e.g., doctor, dentist, physical therapist, etc.), or a combination thereof.

The user device 120 can be any type of electronic device capable of communicating with the form warehouse 120. For example, the user device 120 can be a personal computer, a mobile phone, a tablet, a server with a display, and so on.

The type of medical form data aggregated for the graphical representation can also be based on the type of user of the user device 120. For example, when the user is a medical patient or a user authorized on behalf of the medical patient (e.g., a child for a parent, a parent for a child, etc., another authorized user under HIPAA, etc.), the medical form data can be limited to data included in stored medical forms for that medical patient. In another example, when the user is a healthcare professional such as a physician, the medical form data can be limited to patients which the healthcare professional is, was, or will treat. In yet another example, when the user is a representative or employee of a medical group, hospital or other health care provider, Accountable Care Organization (ACO) or other provider network, third party payer or insurance provider, the medical form data can be limited to patients who are covered by the medical group, hospital or other health care provider, ACO, provider network, third-party payer, or insurance provider.

A generated graphical representation can in some cases be updated with new medical form data. For example, in some cases the form warehouse 105 can store generated graphical representations (e.g., to reduce processing expenditures, etc.). The form warehouse 105 can in some cases receive new medical forms from a medical form feed source (e.g., medical form feed source 110-a and/or 110-b). The form warehouse 105 can extract the medical form data as discussed above and subsequently determine the medical form data is associated with an already generated graphical representation (e.g., the medical form includes a patient identifier that is included in medical form data of a graphical representation). The form warehouse 105 can thus generate an updated graphical representation based on the received medical form(s).

Thus, the graphical representation displays medical form data in a fashion that a patient, healthcare professional, or third-party payer, can understand as a comprehensive medical history at a glance, such as a service a patient has received regardless of location or provider, and at what cost. An important aspect of a health professional's clinical practice is automated and made transparent in a fashion that is not currently available to them—allowing them to see, for each patient, or for a patient population, what was provided, when and where, by whom, and at what cost, all rolled up in a concise, understandable and interactive display. Health professionals can easily visualize the gaps in care, the sequelae of inadequate care coordination, and the impact of inefficient providers. Similarly, patients who receive isolated Explanations of Benefits (EOBs) which, today, are largely incomprehensible, can instead view all the care they have received, consolidated in a meaningful fashion. This will allow patients to better understand the costs of care episodes they experience, reconcile their personal payments with those made by their health insurance plan, and allow them to share this information with their Primary Care Providers (PCPs) and their loved ones. Finally, health professionals and systems administrators can see utilization information for a population of patients in a way which allows them to separate system issues they can impact to improve the quality and reduce the cost of care from unavoidable patient idiosyncrasies.

Figure 2:
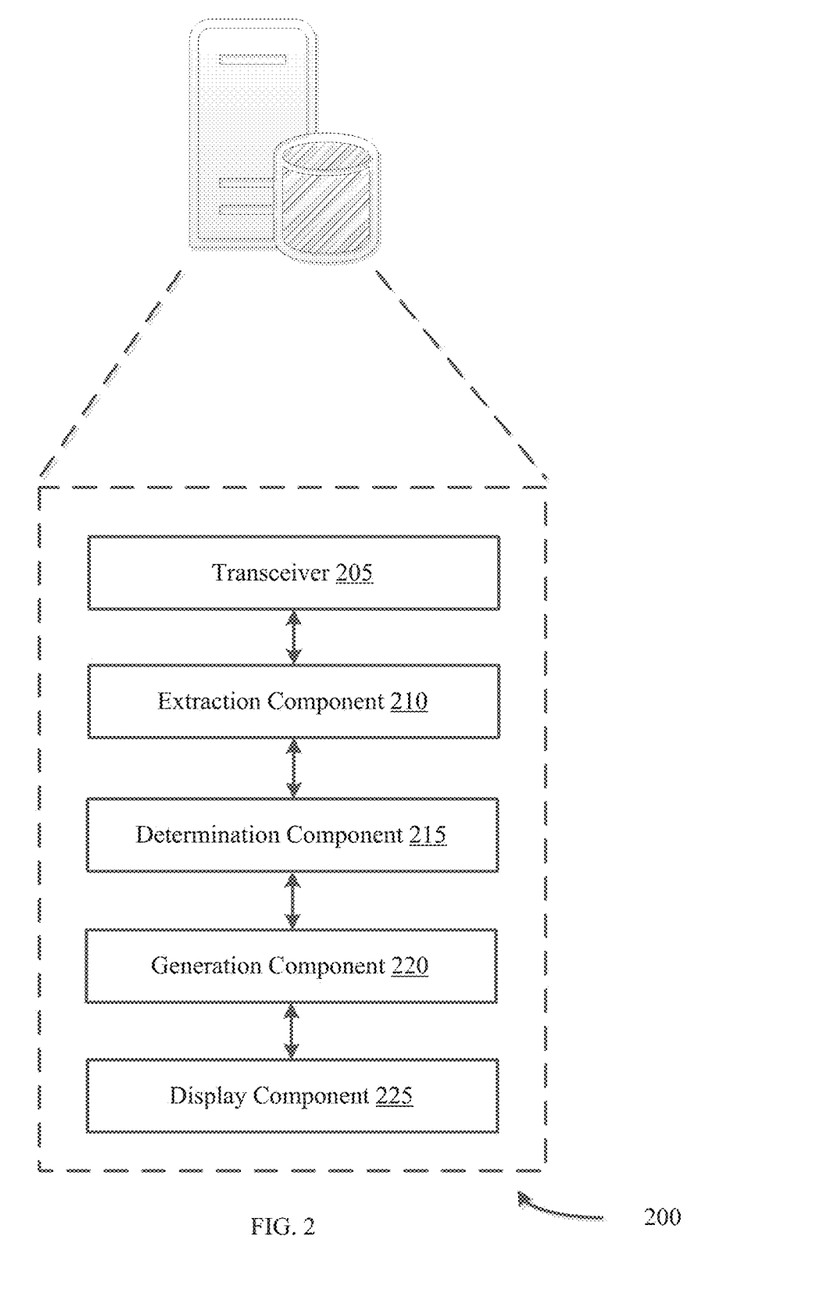
FIG. 2 depicts a data warehouse for displaying medical form information according to an embodiment of the claimed invention.

FIG. 2 depicts a form warehouse 200 for displaying medical form information according to an embodiment of the claimed invention. The form warehouse 200 can be an example of form warehouse 105 as described with reference to FIG. 1. Form warehouse 200 can include a transceiver 205, an extraction component 210, a determination component 215, a generation component 220, and a display component 225.

The transceiver 205 can communicate with other entities across a network system, such as system 100 of FIG. 1. For example, the transceiver can receive and transmit communications to a form source feed (e.g., form source feed 110-*a*, 110-*b*, etc.), a user device (e.g., user device 120), or a combination thereof. For example, the transceiver 205 can receive the medical forms and/or medical form data from a medical form feed source. Additionally or alternatively, the transceiver can transmit a generated graphical representation to a user device. Additionally or alternatively, the transceiver 205 can receive input from the user device, and/or transmit output responses to the user device. In some cases, transceiver 205 can communicate with these various entities via a cloud network (e.g., cloud network 115 of FIG. 1). The transceiver can be composed of a receiver communication chain and a transmitter communication chain. In some cases, the transceiver 205 can be composed of a single communication chain. In some cases, the transceiver 205 can communicate over Internet resources, such as a session over a web browser application.

The extraction component 210 can extract medical form data from medical forms received from at least one form feed source, such as form feed sources 110-*a* and 110-*b* of FIG. 1. For example, the extraction component 210 can execute an Extract, Transform, Load (ETL) mechanism on the received medical forms. The extracted data can subsequently be stored by form warehouse 200.

The determination component 215 can determine associations between medical form data and predefined parameters. The determination can be based on input received from a user device, such as user device 120 of FIG. 1. In some cases, stored medical form data can include embedded data related to the predefined parameters. For example, stored medical form data can include metadata tags or bits indicating an association between the stored medical form data and a predefined parameter. The received input can be selected predefined parameters from a list of predefined parameters. The determination component 215 can search through the stored medical form data and identify the embedded metadata. The determination component 215 can compare the embedded metadata with the predefined parameter.

The generation component 220 can generate a graphical representation of the medical form data based on the determined associations. The generation component 220 can pull medical form data determined to be associated with a predefined parameter (e.g., by the determination component 215), and generate the graphical representation. In some cases, the graphical representation can be a Gantt graph. Further, the graphical representation can in some cases span across all received medical forms for a given patient or given patients.

The display component 225 can display the graphical representation. In some cases, the display can be a graphical user interface (GUI) connected to the form warehouse 200. In some cases, the display component 225 can be connected to a user device, such user device 120 of FIG. 1, where the user device receives the generated graphical representation from the form warehouse 200 and subsequently displays the graphical representation.

Figure 3:
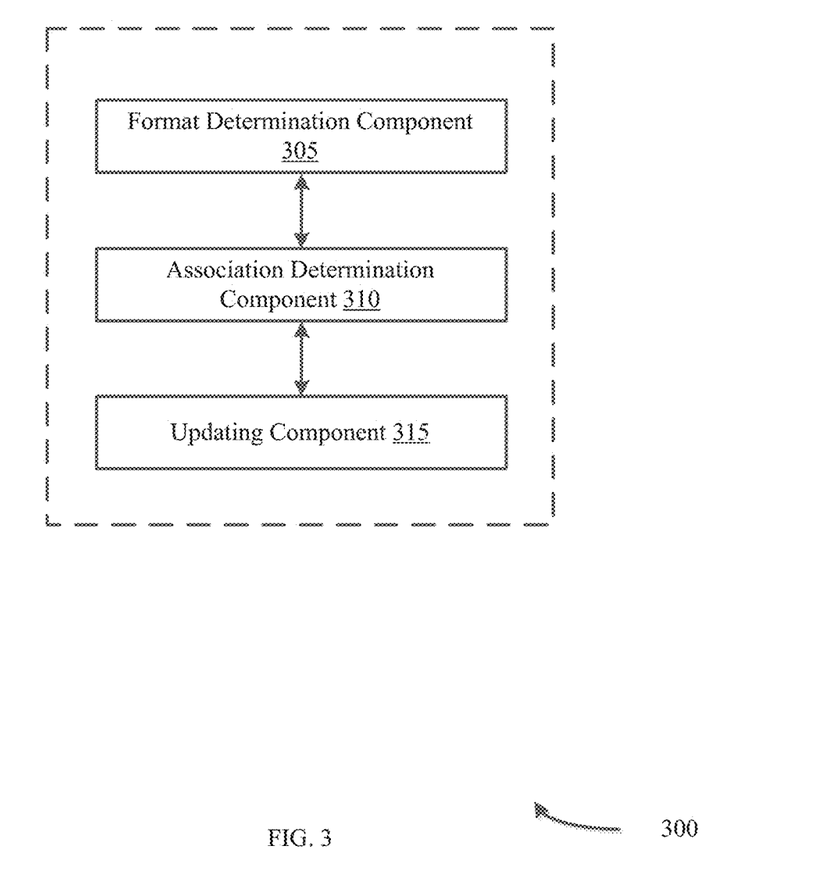
FIG. 3 depicts a determination component of a data warehouse for displaying medical form information according to an embodiment of the claimed invention.

FIG. 3 depicts a determination component 300 according to an embodiment of the claimed invention. The determination component 300 can be an example of determination component 215 as described with reference to FIG. 2. The determination component 300 can include a format determination component 305, an association determination component 310, and an updating component 315.

The format determination component 305 can determine a format type for a received medical form or medical form data from at least one form feed source, such as form feed sources 110-*a* and 110-*b* of FIG. 1. In some cases, the format determination component 305 can determine at least one format characteristic of a received medical form or medical form data, such as a filename extension. Once the format is determined, the format determination component can then notify an extraction component, such as extraction component 210 of FIG. 2, for extracting medical form data.

The association determination component 310 can determine associations between medical form data and predefined parameters. The determination can be based on input received from a user device, such as user device 120 of FIG. 1. The determination component 310 can search through the stored medical form data and identify and compare information from the data (e.g., embedded metadata, etc.) to predefined parameters as discussed with more detail with reference to the determination component 215 of FIG. 2.

The updating component 315 can update a generated graphical representation based on received medical forms or medical form data. The received medical forms or medical form data can be received subsequent to the generation of the graphical representation.

Figure 4:
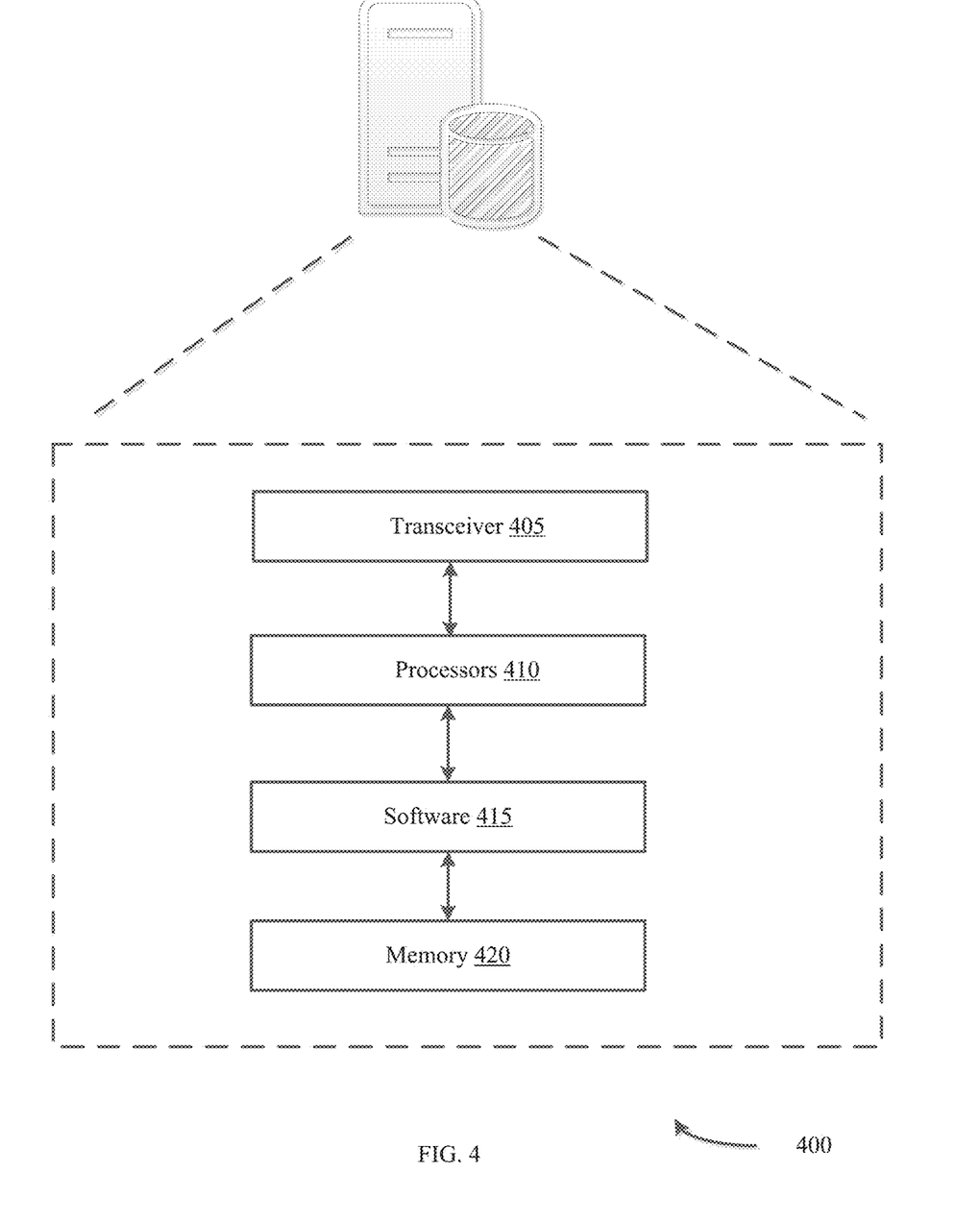
FIG. 4 depicts a data warehouse for displaying medical form information according to an embodiment of the claimed invention.

FIG. 4 depicts a form warehouse 400 according to an embodiment of the claimed invention. The form warehouse 400 can be an example of the form warehouse 200 and/or form warehouse 100 according to FIGS. 2 and 1, respectively. The form warehouse 400 can include a transceiver 405, processors 410, software 415, and memory 420.

Transceiver 405 can communicate with other entities of a system, such as system 100 of FIG. 1. Transceiver 400 can be an example of transceiver 205 as described with reference to FIG. 2.

Processors 410 can execute a set of functions (e.g., included in software 415) of the form warehouse 400. The processors 410 can execute a set of instructions to perform the functions of format determination component 305, the association determination component 310, the updating component 315, the transceiver 205, the extraction component 210, the determination component 215, the generation component 220, the display component 225, or a combination thereof, as described in FIGS. 2 and 3.

Software 415 can include a set of instructions for performing various actions of the form warehouse 400. For example, software 415 can include a set of instructions, that when executed, can perform the functions of format determination component 305, the association determination component 310, the updating component 315, the transceiver 205, the extraction component 210, the determination component 215, the generation component 220, the display component 225, or a combination thereof, as described in FIGS. 2 and 3.

Memory 420 can store the medical forms or medical forms data received from a form feed source, such as form feed source 110-*a* or 110-*b* of FIG. 1. Further, memory 420 can store software for performing the actions of form warehouse 400, such as software 415. Further, the memory 420 can also store graphical representations generated by the form warehouse 400. Additionally or alternatively, memory 420 can also include short-term memory such as random access memory (RAM), long-term memory such as read-only memory (ROM), or a combination thereof.

Example 1

Figure 5:
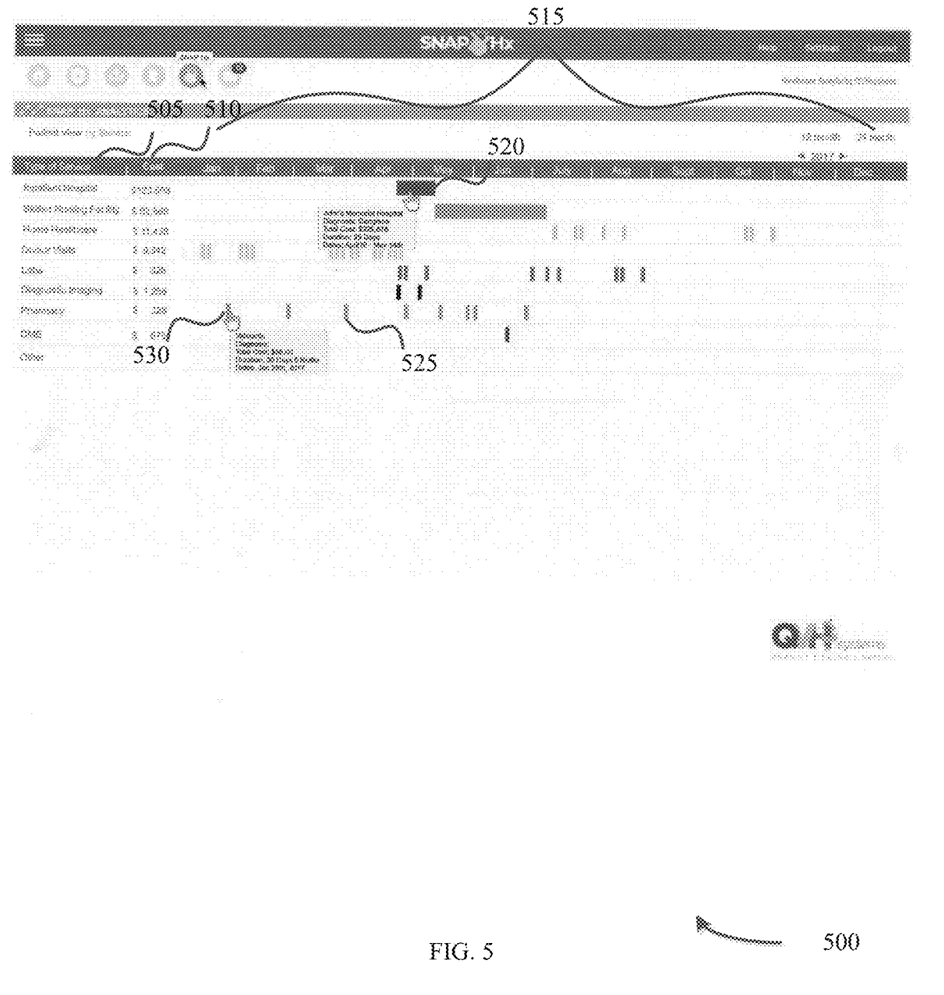
FIGS. 5-7 depict displayed medical history graphs according to embodiments of the claimed invention.

FIG. 5 depicts a displayed graphical representation 500 of a set of medical form data, according to an embodiment of the claimed invention. The displayed graphical representation 500 can be generated by a form warehouse, such as form warehouse 105, 200, or 400, and can be displayed by the form warehouse or a user device (e.g., user device 120).

The graphical representation 500 illustrates a patient's medical data over a specified time period. The graphical representation includes various columns and rows of information. For example, the graphical representation 500 includes a type of service column 505, a cost column 510, and month columns 515. The type of service column 505 includes information related to the type of medical services that the patient receives. For example, rows below the type of service column include services of labs, pharmacy, doctor visits, etc. The cost column 510 includes information related to the costs payed for the type of services the patient received. For example, the patient was charged $1,256 for diagnostic imaging services over the specified time period (e.g., for the year 2017).

The remaining columns 515 are the predefined months for which the graphical representation 500 illustrates data reflecting the medical services the patient received. The monthly columns 515 are arranged in chronological order, and cover a 12 month period from January 2017 to December 2017.

The corresponding rows of the monthly columns depict daily information about medical services received by the patient during the 2017 year. For example, the daily information is partially depicted as rectangular bars, where each rectangular bar is indicative of medical services received by the patient as well as the date(s) that service was received. Each rectangular bar is also color-coded based on the provider of the medical service received. For example, the rectangular bar 520 can be color coded red. The red color code can be associated with the name of the inpatient hospital where the patient received the service, and the length of the bar depicts at a glance how long the service lasted. As another example, the rectangular bar 525 can be color coded orange. The orange color code can be associated with pharmaceutical services the patient received for the 2017 year. Thus, by looking at the graphical representation, one can see at a glance which types of services were received in what order, when multiple services were received in the same day, whether more than one health care provider provided the same type of service, and the total cost of each type of service for the timeframe displayed.

The graphical representation 500 can also display additional information related to the daily medical services (e.g., that are depicted as rectangular bars). For example, a user can click or hover a pointer of a device over a rectangular bar, and an additional window can open displaying additional medical information corresponding to that rectangular bar. For example, the opened window pertaining to the rectangular bar 530 displays the name of the drug, diagnosis information, total cost information, duration information, and the date the drug was dispensed.

Example 2

Figure 6:
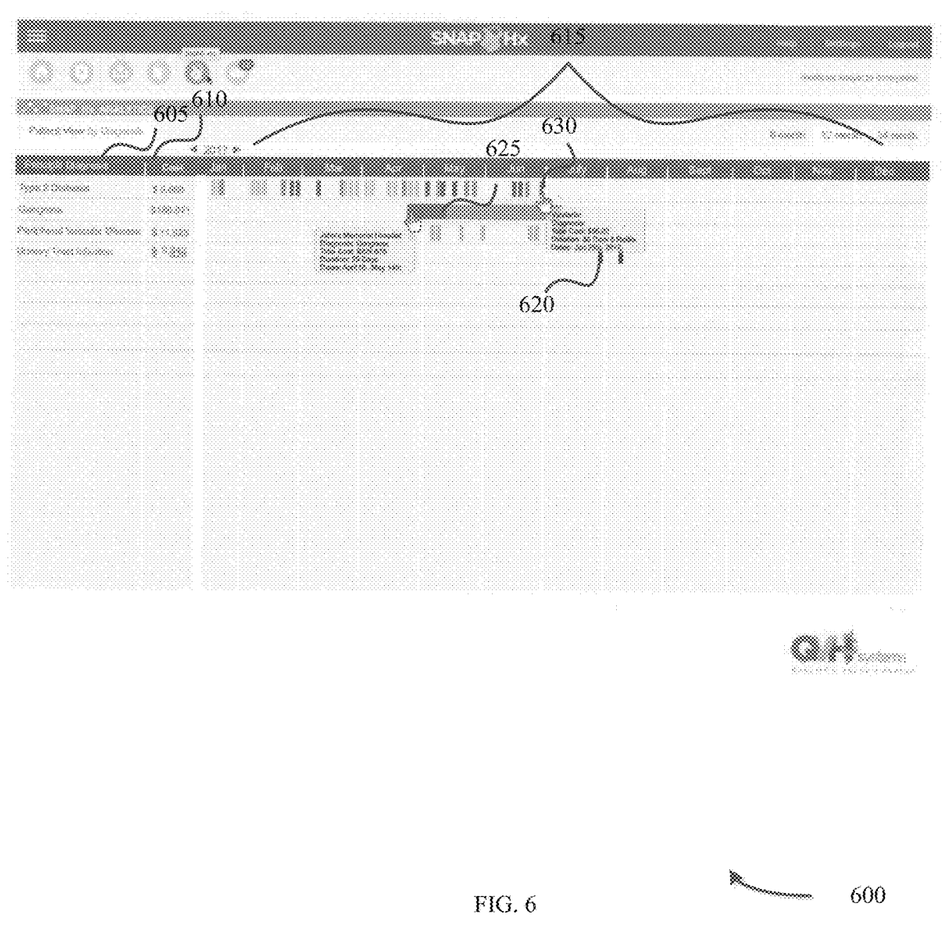

FIG. 6 depicts a displayed graphical representation 600 of a set of medical form data, according to an embodiment of the claimed invention. The displayed graphical representation 600 can be generated by a form warehouse, such as form warehouse 105, 200, or 400, and can be displayed by the form warehouse or a user device (e.g., user device 120).

The graphical representation 600 illustrates a patient's medical data over a specified time period. The graphical representation 600 includes a principle diagnosis column 605, a cost column 610, and month columns 615. The principle diagnosis column 605 includes information related to any medical diagnoses that the patient receives. For example, rows below the principal diagnosis column include type 2 diabetes, gangrene, etc. The cost column 610 includes information related to the costs payed for the type of services the patient received associated with the corresponding diagnosis. For example, the patient was charged $11,925 for medical services related to the corresponding diagnosis of peripheral vascular disease over the specified time period.

The remaining columns 615 are the predefined months for which the graphical representation 600 illustrates data for. The monthly columns 615 are arranged in chronological order and cover a 12 month period from January 2017 to December 2017.

The corresponding rows of the monthly columns depict daily information about medical services received by the patient corresponding to the associated diagnosis during the 2017 year. The daily information is partially depicted as rectangular bars, where each rectangular bar is indicative of medical services received for a particular day. For example, rectangular bar 620 corresponds to medical services the patient received during a day in July and pertaining to the diagnosis of urinary tract infection.

Each rectangular bar is also color-coded based on the type of medical service received. For example, the rectangular bar 625 can be color coded red. The red color code can be associated with the name of the inpatient hospital where the patient was hospitalized, and the length of the bar shows the length of that hospitalization. As another example, the rectangular bar 630 can be color coded blue. The blue color code can be associated with a particular prescription drug the patient received for the 2017 year.

The graphical representation 600 can also display additional information related to the daily medical services depicted as rectangular bars. A user can click or hover a pointer of a device over a rectangular bar, and an additional window can open displaying additional medical information corresponding to that rectangular bar. For example, the opened window pertaining to the rectangular bar 625 displays service location, diagnosis information, total cost information, duration information, and date information for the medical services received for the corresponding days. By looking at the graphical representation, one can see at a glance which types of services were received in what order for each diagnosis, when multiple services were received on the same day, whether more than one health care provider provided the same type of service, and the total cost of each diagnosis for the timeframe displayed.

Example 3

Figure 7:
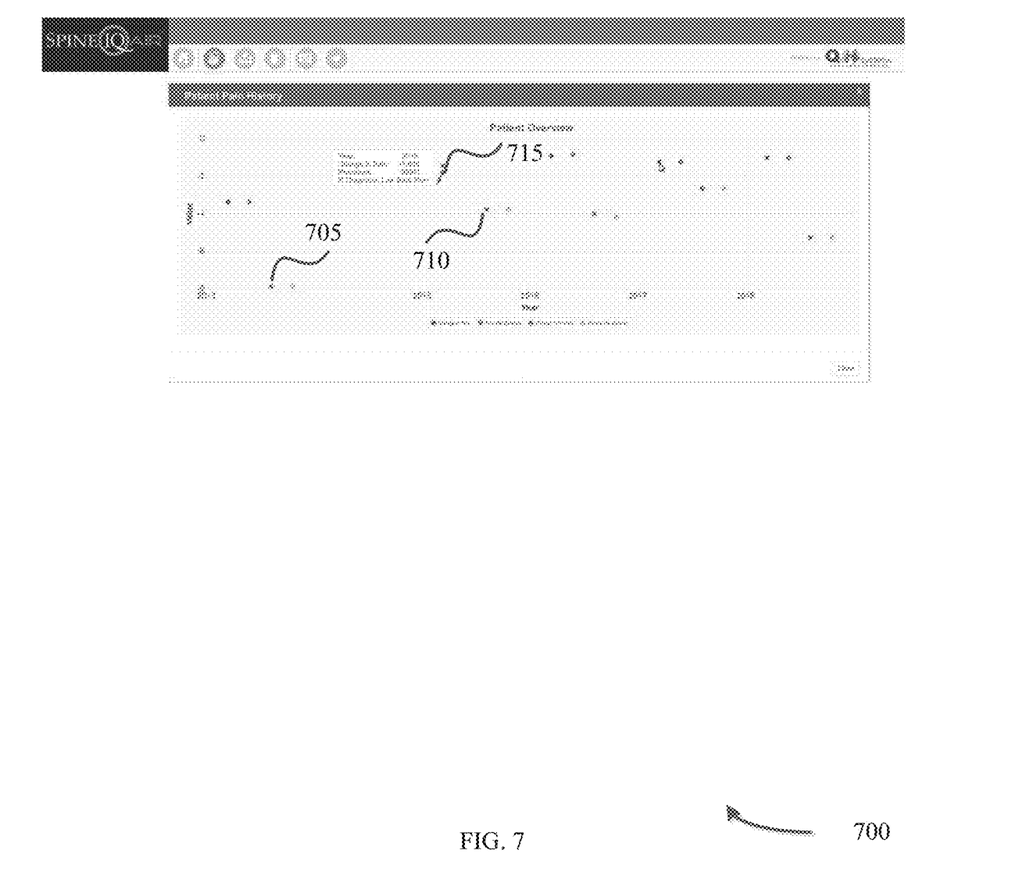

FIG. 7 depicts a displayed graphical representation 700 of a set of medical form data, according to an embodiment of the claimed invention. The displayed graphical representation 700 can be generated by a form warehouse, such as form warehouse 105, 200, or 400, and can be displayed by the form warehouse or a user device (e.g., user device 120).

The graphical representation 700 illustrates data points in chronological order and over a specified time period relating to a patient's medical data. The graphical representation 700 includes different data point types, including a change in pain data type, a pain per episode data type, a change in Patient-Reported Outcomes Measurement Information System (PROMIS) data type, and a PROMIS per episode data type. One axis is a continuous, chronological timeline (e.g., from the years 2013-2018), while the other axis can be a relative value.

The values for data points illustrated in the graphical representation can be relative to adjacent data points of the same type. For example, the value for the data point 710 is −4. The value for the data point can be based on the value of the data point 705 (e.g., having a relative value approximately equal to −8), which came chronologically before the data point and is the same data type of a change in PROMIS value. Thus, when a user views the change in PROMIS data points, the user can see trends of a patient's health as time passes (e.g., the patient experienced a relative increase in PROMIS value between 2013 and 2016).

Similar to the other examples in FIGS. 5 and 6, the graphical representation can display additional information associated with the data points. For example, when a user either clicks the data point 715 or hovers a mouse icon over the data point 715, a new window can be displayed providing additional information associated with that data point. For example, the new window can show information such as the year the patient received medical service, the relative value for the change in pain, a procedure identifying number, a primary diagnosis type, and the like.

It should be noted that any of graphical representations 500-700 of FIGS. 5-7 can be generated in a variety of scenarios. The graphical representations depicted can be originally generated representations, for example, when an end user requests the generation of the representation for the first time. In some cases, the graphical representations depicted can be modified based on selected inputs (e.g., parameters or categories) from the end user subsequent to the display of a previously generated graphical representation. In some cases, the graphical representations depicted can be updated dynamically based on newly received medical form/information from various medical form feeds.

Furthermore, the depicted graphical representations contain a variety of parameters, conditions, and/or associations. Different visual indicators can also be used. For example, the colors discussed in Examples 1-4 above are not limited to the specific colors used, nor the use of colors. While instructive, the claimed invention is not limited to these depicted parameters, conditions, and/or associations. The depicted graphical representations are also displayed in specific formatting. For example, FIGS. 5-7 include displayed "buttons" in the top-left corner of the graphical representations, which can be used by an end user to update and/or modify the displayed graphical representation. While instructive, the claimed invention is not limited to these depicted display formatting, and any formatting can be used for displaying the graphical representations.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method comprising:
   receiving a plurality of digital patient forms from at least one medical feed source, where each digital patient form comprises a set of medical data for a medical patient;
   identifying a format of the received plurality of digital patient forms;
   extracting the medical data from the plurality of digital patient forms based at least in part on the identified format;
   determining at least a portion of medical data from the plurality of digital patient forms is associated with a predefined medical parameter, where the predefined medical parameter is different than a temporal parameter;
   generating a graphical medical history of the at least a portion of medical data, the graphical medical history organized by a categorical variable axis and providing a visual indicator of the association between the at least a portion of medical data and the predefined medical parameter temporally spanning across the plurality of digital patient forms; and
   displaying the graphical medical history via a graphical user interface (GUI) to a user, wherein the graphical medical history is displayed as data points, and
   wherein values corresponding to the data points can be represented as relative values to the adjacent data points of the same type.

2. The method of claim 1, wherein the visual indicator comprises a color or an object shape representing a medical event.

3. The method of claim 1, wherein the graphical medical history further comprises a Gantt graph.

4. The method of claim 1, further comprising:
   receiving input from the user selecting the predefined medical parameter; wherein the determining is based at least in part on the received input.

5. The method of claim 1, wherein the predefined medical parameter comprises a type of medical condition, a type of diagnosis, a type of medical service, a type of medical service provider, a medical prognosis, or a combination thereof.

6. The method of claim 1, wherein the user comprises the patient, a health care provider, an insurance provider representative, an authorized user for the health care provider, an authorized user for a health care provider organization, or an authorized user for the patient.

7. The method of claim 1, further comprising:
   receiving a second plurality of digital patient forms comprising a second set of medical data for another medical patient;
   determining at least a portion of the second set of medical data is associated with the predefined medical parameter; and wherein the graphical medical history further provides a visual indicator of the association between the at least a portion of the second set of medical data and the predefined medical parameter temporally spanning across the second plurality of digital patient forms.

8. The method of claim 1, further comprising:
   receiving at least one additional digital patient form from the at least one form feed source; and
   updating the graphical medical history of the at least a portion of medical data based on the at least one additional digital patient form.

9. A system, comprising:
- a form data storage component in electronic communication with at least one form feed source, the form data storage component configured to receive a plurality of digital patient forms from the at least one form feed source, where each digital patient form comprises a set of medical data for a medical patient;
- an extraction component configured to extract the medical data from the plurality of digital patient forms,
- a form analysis component configured to:
  - determine at least a portion of medical data from the plurality of digital patient forms is associated with a predefined medical parameter; and
  - generate a graphical medical history of the at least a portion of medical data, the graphical medical history organized by a categorical variable axis and providing a visual indicator of the association between the at least a portion of medical data and the predefined medical parameter temporally spanning across the plurality of digital patient forms; and
- a graphical user interface (GUI) configured to display the graphical medical history to a user, wherein the graphical medical history is displayed as data points, and wherein values corresponding to the data points can be represented as relative values to the adjacent data points of the same type.

10. The system of claim 9, wherein the visual indicator comprises a color, an object shape, or text representing a medical event.

11. The system of claim 9, wherein the graphical medical history further comprises a Gantt graph.

12. The system of claim 9, wherein the form analysis component is further configured to receive input from the user selecting the predefined medical parameter; wherein the determining is based at least in part on the received input.

13. The system of claim 9, wherein the predefined medical parameter comprises a type of medical condition, a type of diagnosis, a type of medical service, a type of medical service provider, a medical prognosis, or a combination thereof.

14. The system of claim 9, wherein the user comprises the patient, a medical provider, an insurance provider representative, an authorized user for the health care provider, an authorized user for a health care provider organization, or an authorized user for the patient.

15. The system of claim 9, wherein the form analysis component is further configured to:
- receive a second plurality of digital patient forms comprising a second set of medical data for another medical patient;
- determine at least a portion of the second set of medical data is associated with the predefined medical parameter; and wherein the graphical medical history further provides a visual indicator of the association between the at least a portion of the second set of medical data and the predefined medical parameter temporally spanning across the second plurality of digital patient forms.

16. A non-transitory computer readable medium comprising computer readable program code that, when executed, causes a processor to:
- receive a plurality of digital patient forms from at least one form feed source, where each digital patient form comprises a set of medical data for a medical patient;
- identifying a format of the received plurality of digital patient forms;
- extracting the medical data from the plurality of digital patient forms based at least in part on the identified format;
- determine at least a portion of medical data from the plurality of digital patient forms is associated with a predefined medical parameter;
- generate a graphical medical history of the at least a portion of medical data, the graphical medical history organized by a categorical variable axis and providing a visual indicator of the association between the at least a portion of medical data and the predefinedmedical parameter temporally spanning across the plurality of digital patient forms; and
- display the graphical medical history via a graphical user interface (GUI) to a user wherein the graphical medical history is displayed as data points, and wherein values corresponding to the data points can be represented as relative values to the adjacent data points of the same type.

17. The non-transitory computer readable medium of claim 16, wherein the visual indicator comprises a color, an object shape, or text representing a medical event.

18. The non-transitory computer readable medium of claim 16, wherein the graphical medical history further comprises a Gantt graph.

19. The non-transitory computer readable medium of claim 16, wherein the computer readable program code is further executable to:
- receive input from the user selecting the predefined medical parameter;

wherein the determining is based at least in part on the received input.

* * * * *